United States Patent
Ramsey

(10) Patent No.: US 10,182,705 B2
(45) Date of Patent: Jan. 22, 2019

(54) GRIPPING DEVICE

(71) Applicant: Meditech Endoscopy Ltd, Derbyshire (GB)

(72) Inventor: Peter Ramsey, Derbyshire (GB)

(73) Assignee: MEDITECH ENDOSCOPY LTD, Derbyshire (GB)

(*) Notice: Subject to any disclaimer, the term of this patent is extended or adjusted under 35 U.S.C. 154(b) by 182 days.

(21) Appl. No.: 15/036,269

(22) PCT Filed: Nov. 17, 2014

(86) PCT No.: PCT/GB2014/053390
§ 371 (c)(1),
(2) Date: May 12, 2016

(87) PCT Pub. No.: WO2015/071688
PCT Pub. Date: May 21, 2015

(65) Prior Publication Data
US 2016/0296105 A1    Oct. 13, 2016

(30) Foreign Application Priority Data

Nov. 18, 2013 (GB) .................................. 1320336.9
Jul. 16, 2014 (GB) .................................. 1412662.7

(51) Int. Cl.
*A61B 1/00* (2006.01)
*A61B 1/005* (2006.01)

(52) U.S. Cl.
CPC ........ *A61B 1/00154* (2013.01); *A61B 1/0052* (2013.01); *A61B 1/00103* (2013.01); *A61B 1/00135* (2013.01); *A61B 1/00137* (2013.01)

(58) Field of Classification Search
CPC .............. A61B 1/00154; A61B 1/0052; A61B 1/00135; A61B 1/00103; A61B 1/00137;
(Continued)

(56) References Cited

U.S. PATENT DOCUMENTS

| 5,382,239 A | * | 1/1995 | Orr | ....................... A61M 25/02 604/177 |
| 5,976,075 A |   | 11/1999 | Beane et al. | |

(Continued)

FOREIGN PATENT DOCUMENTS

| EP | 0521590 A1 | 6/1992 |
| EP | 1704822 A1 | 3/2006 |

(Continued)

*Primary Examiner* — Timothy J Neal
(74) *Attorney, Agent, or Firm* — Hayes Soloway PC

(57) ABSTRACT

This invention relates to a gripping device for an endoscope, and to an assembly comprising an endoscope and a gripping device. A single use gripping device for an endoscope shaft comprises a first part; a second part, the second part being moveable relative to the first part, and at least one of the first and second parts including a channel for receiving said shaft, the second part being moveable relative to the first part between a first, open configuration in which the endoscope shaft can be placed in the channel and a second, closed configuration in which, in use, the first and second parts surround said endoscope shaft; engaging means configured to retain the first and second parts in said closed configuration and to prevent movement of the first and second parts back to said open configuration without disabling the engaging means; and detent means arranged to prevent insertion of an endoscope shaft into said channel when, in use, the first and second parts are in said closed configuration.

10 Claims, 10 Drawing Sheets

(58) Field of Classification Search
CPC .............. A61B 1/0014; A61B 1/00112; A61B 1/00121; A61B 1/00062; A61B 1/00101
See application file for complete search history.

(56) References Cited

U.S. PATENT DOCUMENTS

| | | | |
|---|---|---|---|
| 6,981,945 B1 * | 1/2006 | Sarvazyan | A61B 1/00147 600/131 |
| 2003/0187326 A1 | 10/2003 | Chang | |
| 2003/0212308 A1 | 11/2003 | Bendall | |
| 2008/0287739 A1 | 11/2008 | Smith et al. | |
| 2009/0026682 A1 | 1/2009 | Smith et al. | |
| 2009/0247827 A1 | 10/2009 | Secrest et al. | |
| 2011/0065991 A1 | 3/2011 | Sarvazyan et al. | |
| 2011/0065992 A1 | 3/2011 | Bissinger | |

FOREIGN PATENT DOCUMENTS

| | | |
|---|---|---|
| EP | 1982637 A1 | 4/2008 |
| GB | 2455343 A | 6/2009 |
| JP | 2283345 A | 11/1990 |
| WO | 2004021868 A2 | 3/2004 |
| WO | 2005099558 A1 | 10/2005 |
| WO | 20061300730 A2 | 7/2006 |
| WO | 2007059564 A1 | 5/2007 |
| WO | 2008144630 A2 | 11/2008 |

* cited by examiner

GRIPPING DEVICE

BACKGROUND a. Field of the Invention

This invention relates to a gripping device for an endoscope, to an assembly comprising an endoscope and a gripping device, and to a method of aiding grip of an endoscope shaft.

b. Related Art

Endoscopes comprise an elongate shaft or insertion tube and a control head containing angulation controls and valves. During an endoscopic procedure the shaft, which is coated in a suitable lubricant, is inserted slowly into a patient in order to visualise the internal cavity being examined. In preferred methods of use, endoscopists grip the shaft in one hand while operating the controls of the control head with the other hand. The endoscopist must be able to grip the shaft firmly enough to manipulate the shaft, while also being able to slide their hand along the shaft as the shaft is inserted further into the patient.

The shaft is preferably held between the thumb and fingers as this finger grip allows more feel and control over the movements of the shaft. Additionally, it is recommended that a piece of gauze is placed between the shaft and the user's thumb and fingers to provide greater friction and avoid slippage due to the lubricant.

However, the piece of gauze quickly becomes saturated with lubricant, substantially decreasing its benefits to the user. Furthermore, if it is necessary for the user to remove their hand from the endoscope shaft, there is a high likelihood that the gauze will slip from around the shaft and possibly fall to the floor.

In colonoscopies, as the endoscope or colonoscope is progressed around bends or loops in the patient's colon there may come a point where the pushing force of the operator is not being transmitted along the longitudinal axis of the colonoscope and the colonoscope itself can form a loop. This can cause discomfort to the patient and can prevent progress of the scope through the colon, as any force applied to the colonoscope will only tend to increase the loop effect.

Looping is remedied by twisting or applying a torque force (torquing) to the shaft of the colonoscope whilst pulling back on the colonoscope shaft. This undoes the loop and allows subsequent progression through the colon.

Due to the amount of force required to torque the shaft, its lubricious nature and the way it is generally held, however, the endoscopist can experience significant pain and discomfort in their hands and wrist.

It is known that endoscopists can suffer from a number of musculoskeltal injuries caused by the prolonged gripping or pinching forces that are exerted by the user's hand on the endoscope during use. These injuries include wrist tendinopathy, epicondylitis and carpal tunnel syndrome, and can cause numbness of the hands, as well as pain in the hands, wrists and forearms of the user.

It is, therefore, an aim of the present invention to provide a gripping device for an endoscope shaft that overcomes the above mentioned problems.

SUMMARY OF THE INVENTION

This invention relates in general to a gripping device for an endoscope shaft comprising gripping means, a first part, and a second part, the second part being moveable relative to the first part, and at least one of the first and second parts including a channel for receiving the shaft, wherein, the second part is moveable relative to the first part between a first position in which the gripping means is engaged with the endoscope shaft and a second position in which the gripping means is disengaged from the endoscope shaft to allow the gripping device to be slid along the shaft.

The gripping device of the present invention is preferably designed such that when the device is engaged around an endoscope shaft it remains secured around the shaft even when a user's grip on the device is released. Accordingly in preferred embodiments of the invention, when the first and second parts are in the first position no sliding of the endoscope shaft with respect to the device is possible, and when the first and second parts are in the second position sliding of the device with respect to the shaft is possible but the device is retained around the shaft.

Furthermore, the device preferably includes one or more features that limit the force that can be applied to the endoscope shaft by the device, thereby preventing damage to the shaft.

According to a first aspect of the present invention there is provided a single use gripping device for an endoscope shaft, the gripping device comprising:

a first part;

a second part, the second part being moveable relative to the first part, and at least one of the first and second parts including a channel for receiving said shaft, the second part being moveable relative to the first part between a first, open configuration in which the endoscope shaft can be placed in the channel and a second, closed configuration in which, in use, the first and second parts surround and are retained around said endoscope shaft;

engaging means configured to retain the first and second parts in said closed configuration;

gripping means provided on at least one of the first part and the second part, said gripping means configured such that when the gripping device is in its closed configuration the first and second parts are movable relative to each other between a first position in which the gripping means does not grip an endoscope shaft positioned in the channel to allow the gripping device to be slid along said shaft and a second position in which the gripping means grips said endoscope shaft; and means configured to prevent said gripping device being engaged around a second endoscope shaft after the device has been engaged around and removed from a first endoscope shaft.

A single-use feature configured such that, in use, when the gripping device has been removed from the endoscope after a first use it cannot be repositioned and/or retained around a second endoscope shaft beneficially prevents the device being used in multiple endoscopic procedures, which may lead to cross-contamination.

In some embodiments the means configured to prevent said gripping device being engaged around a second endoscope shaft comprises a part of the engaging means arranged such that, in use, after the first and second parts have been engaged in said closed configuration, the first and second parts cannot be moved back to said open configuration without disabling the engaging means.

The means configured to prevent said gripping device being engaged around a second endoscope shaft may comprise detent means arranged to prevent insertion of an endoscope shaft into said channel when, in use, the first and second parts are in said closed configuration.

In preferred embodiments the first and second parts, in their closed configuration, form a substantially cylindrical main body of the device defining a longitudinal axis of the device. The outer diameter of this main body is, advantageously, significantly greater than the outer diameter of the endoscope shaft. In this way, the stresses on a user's hand and wrist are decreased when a user grips the device, compared to gripping the shaft directly, while still applying the same torque to the endoscope shaft. Preferably the first and second parts are hingedly connected along a longitudinal edge of each of the first and second parts. This enables the first and second parts to be clamped or closed around the endoscope shaft.

In preferred embodiments the first and second parts are biased in the first position. As such, when a user releases or decreases their grip on the device, the first and second parts move to the first position in which the device does not grip the endoscope shaft. In alternative embodiments the first and second parts may be biased in the second position.

Preferably the gripping means comprises protrusions extending into the channel. The protrusions may be made from an elastomeric material.

The engaging means preferably comprises complementary hook portions on each of the first and second parts.

Preferably the detent means comprises an arm member biased to extend into the channel. The arm member may be integrally formed with the first part or the second part. In particularly preferred embodiments the first and second parts define first and second ends of the gripping device and the detent means comprises two arm members, and wherein a first arm member extends into said channel in a direction substantially towards said first end and a second arm member extends into said channel in a direction substantially towards said second end.

The first and second parts, in their closed configuration, preferably form a substantially cylindrical main body of the device having first and second ends, and the gripping device preferably further comprises an end cap securable to said first end. The end cap may include one or more holes sized to permit liquid to pass through said end cap.

Preferably the main body has a first end and a second end, and the gripping device preferably further comprises a wiping element proximate at least one of the first or second end for removing lubricant or other liquid from around the endoscope shaft. This reduces the amount of lubricant that gets between the gripping element and the endoscope shaft, which would reduce the gripping force of the gripping device.

In some embodiments at least one of a first and second end of the main body comprises a flanged end portion. The flanged end portion preferably extends in a generally outwardly direction relative to the endoscope shaft when the gripping device is secured around the endoscope shaft. This flanged end portion is designed to minimise the amount of lubricant or other liquid that is transferred to the outer surface of the device during use.

The channel typically defines a longitudinal axis of the device. In some embodiments the second part is moveable relative to the first part in a direction perpendicular to the axis. In other embodiments the second part is moveable relative to the first part in a direction parallel to the axis. Ideally the gripping device is designed to be manipulated single-handedly by a user.

In preferred embodiments the gripping means comprises an elastomeric material. The elastomeric material is preferably provided on a first surface of the first part such that, in use, elastomeric material is located between the first part and the endoscope shaft. Alternatively or additionally, elastomeric material may be provided on a first surface of the second part such that, in use, elastomeric material is located between the second part and the endoscope shaft. Preferably the elastomeric material is formed as discrete protrusions.

In other embodiments, the gripping means may comprise a gripping element having a substantially circular aperture, a radius of the aperture lying in a plane of the gripping element. In these embodiments the gripping element is preferably tiltable between a first position in which the plane of the gripping element is at a first angle with respect to the longitudinal axis and a second position in which the plane of the gripping element is at a second angle with respect to the longitudinal axis as the second part is moved relative to the first part between the first position and the second position, the second angle being greater than the first angle.

According to a second aspect of the present invention there is provided an assembly comprising an endoscope and a gripping device according to the first aspect of the invention, the gripping device being secured around the shaft of the endoscope.

According to a third aspect of the present invention there is provided a gripping device for an endoscope shaft, the gripping device comprising:

a main body having first and second ends, the main body having a first part and a second part, the second part being moveable relative to the first part between a first, open configuration and a second, closed configuration;

a channel in at least one of the first and second parts extending between said first and second ends, the channel configured such that in said open configuration the endoscope shaft can be placed in the channel and in said closed configuration, in use, the first and second parts surround said endoscope shaft;

engaging means configured to retain the first and second parts in said closed configuration;

gripping means provided on at least one of the first part and the second part, said gripping means configured such that when the gripping device is in its closed configuration the first and second parts are movable relative to each other between a first position in which the gripping means does not grip an endoscope shaft positioned in the channel to allow the gripping device to be slid along said shaft and a second position in which the gripping means grips said endoscope shaft; and an end cap removably secured to said first end of the main body.

Preferably the end cap includes one or more holes sized to permit liquid to pass through said end cap.

The gripping device may be single use and in these embodiments a part of the engaging means may be configured such that, in use, after the first and second parts have been engaged in said closed configuration, the first and second parts cannot be moved back to said open configuration without disabling the engaging means. Alternatively or additionally the device may further comprise detent means arranged to prevent insertion of an endoscope shaft into said channel when, in use, the first and second parts are in said closed configuration.

In some embodiments a longitudinal axis of the main body extends between said first and second ends, and the first and second parts are hingedly connected along a longitudinal edge of each of the first and second parts.

The first and second parts may be biased in the first position.

In preferred embodiments the end cap is configured such that when the end cap is engaged with the end of the main body, the first and second parts of the main body are retained in the second position of the closed configuration.

According to a fourth aspect of the present invention there is provided an assembly comprising an endoscope and a gripping device according to the third aspect of the invention, the gripping device being secured around the shaft of the endoscope such that the main body of the gripping device extends over and protects the distal tip portion of the endoscope.

According to a fifth aspect of the present invention there is provided a method of aiding grip of an endoscope shaft, the method comprising:
  securing a gripping device according to the first aspect of the invention around the shaft of the endoscope; and
  moving the first and second parts relative to each other into the second position.

According to a sixth aspect of the present invention there is provided a method of aiding grip of an endoscope shaft, the method comprising:
  securing a gripping device according to the third aspect of the invention around the shaft of the endoscope; and
  moving the first and second parts relative to each other into the second position.

BRIEF DESCRIPTION OF THE DRAWINGS

The invention will now be further described by way of example only and with reference to the accompanying drawings, in which.

DETAILED DESCRIPTION

Figure 1:
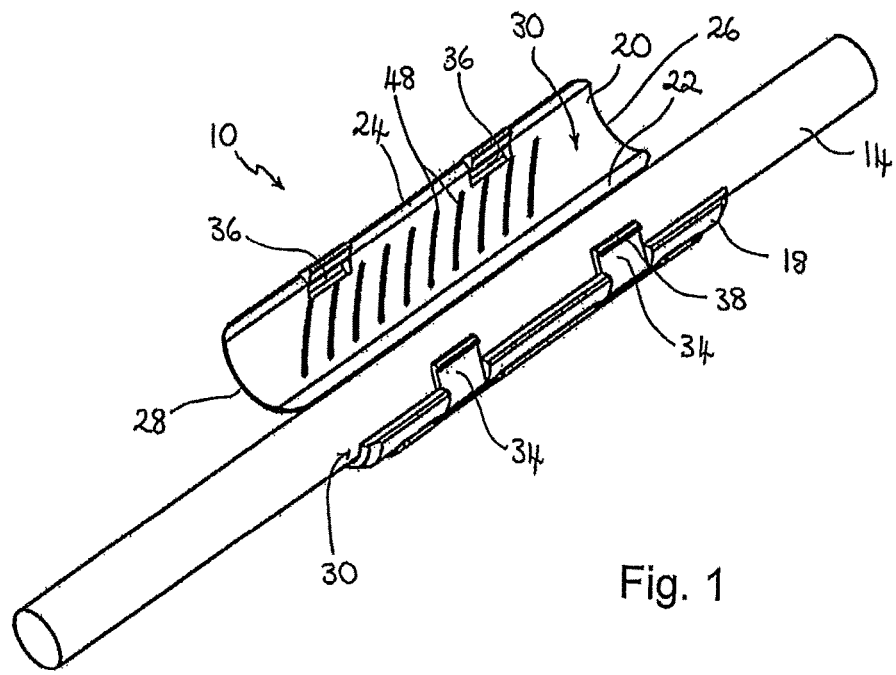
FIG. 1 is a perspective view of a gripping device according to a first preferred embodiment of the present invention in an open configuration.
Figure 2:
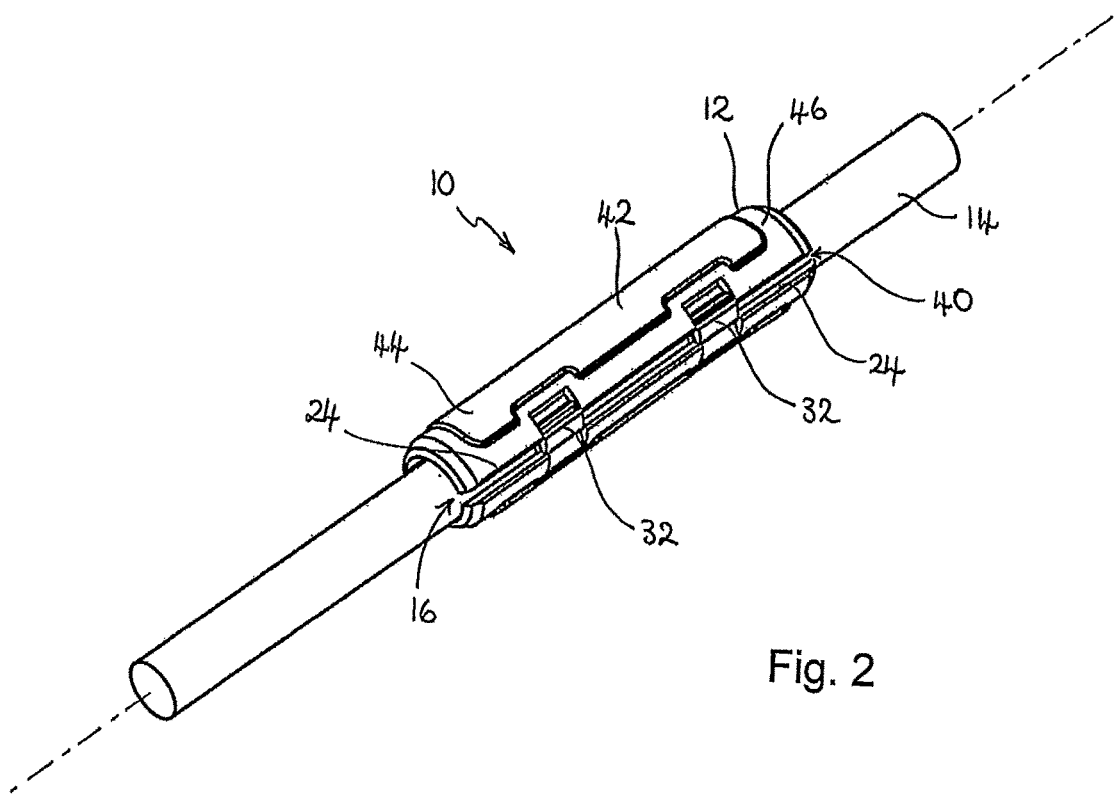
FIG. 2 is a perspective view of the gripping device of FIG. 1 in a closed configuration around an endoscope shaft.

FIGS. 1 and 2 show a gripping device 10 according to a first preferred embodiment of the present invention. The gripping device 10 comprises a main body 12 that, in use, at least partially surrounds a shaft 14 of an endoscope to retain the device 10 on the shaft 14.

The main body 12 is substantially cylindrical or tubular and includes a longitudinal bore 16 for receiving the shaft 14 of the endoscope. In this example the main body 12 comprises a first part 18 and a second part 20 that are hingedly connected. Each of the first and second parts 18, 20 has a half-pipe shape, such that a cross-section perpendicular to a longitudinal axis of each part is substantially semi-circular. Parallel long edges 22, 24 extend between respective first and second ends 26, 28 of each of the first and second parts 18, 20. In this way, a channel 30 is formed in each of the first and second parts 18, 20 for receiving the endoscope shaft 14.

The first and second parts 18, 20 are hingedly connected along respective first long edges 22. In this example the hinge is a natural hinge formed in the material from which the main body 12 is made.

Each of the first and second parts 18, 20 comprises securing means 32 for securing the main body 12 in a closed configuration. The securing means 32 are located proximate or along the second long edge 24 of each of the parts 18, 20. As shown most clearly in FIG. 1, the securing means 32 on the first part 18 comprises tab members 34 and the securing means 32 on the second part 20 comprises corresponding apertures 36 for receiving the tab members 34. The tab members 34 include barbed end portions 38 that allow the tab members 34 to be inserted through the apertures 36 in a first direction to secure the first and second parts 18, 20 together, but which prevent the tab members 34 being withdrawn in a second direction.

The tab members 34 and apertures 36 are configured such that, when engaged, the second long edges 24 of the first and second parts 18, 20 are proximate each other, but some relative movement of the first and second parts 18, 20 is still possible. In particular it is preferable if, when the securing means 32 are engaged, there is a gap 40 between the second long edges 24 of the first and second parts 18, 20 and that the width of the gap 40 may be decreased by squeezing or pressing the first and second parts 18, 20 together around the endoscope shaft 14. In this way, the greater the force applied to the first and second parts 18, 20 by a user, the smaller the gap 40 between the first and second parts 18, 20 becomes and the greater the gripping force that is applied to the endoscope shaft 14.

In some embodiments the gap 40 may fully close, so that the second long edges 24 are in touching contact, when sufficient force is applied to the first and second parts 18, 20. This limits the gripping force that can be applied to the endoscope shaft 14, thereby minimising the likelihood of damaging the shaft 14.

It will be appreciated that although two tab members 34 and two apertures 36 have been illustrated in the embodiment shown in FIGS. 1 and 2, in other embodiments only one tab member 34 and one aperture 36 may be provided, or more than two tab members 34 and apertures 36 may be provided. Furthermore, in some embodiments the first and second parts 18, 20 may be fully separable. In this way, securing means 32 may be provided on both of the first and second long edges 22, 24 of the first and second parts 18, 20.

The main body 12 is preferably made from a substantially rigid plastics material such as polypropylene.

The gripping device 10 further comprises gripping means 42 in the form of a layer of elastomeric material 44. In this example the elastomeric material is provided on an outer surface 46 of the main body 12. A plurality of apertures 48 formed in the second part 20 allows a portion of the elastomeric material 44 to protrude through the apertures 48 when a user grips the device 10. The apertures 48 are elongate slits and the elastomeric material that protrudes through the apertures 48, therefore, forms a series of deformable ribs (not shown) extending or protruding into the bore 16 of the gripping device 10. The elastomeric ribs contact the surface of the endoscope shaft 14 and provide grip as a user squeezes the gripping device 10.

The surface area of the deformable ribs is significantly less that the internal surface area of the main body 12 and, accordingly, greater local pressure can be exerted on the endoscope shaft 14 for a given gripping force exerted by the user.

The deformability of the elastomeric material means, however, that there is a limit to the pressure that can be applied before the ribs deform. A further advantage of the deformable ribs is that they are able to at least partially penetrate a layer of lubricant coating the shaft 14 and, therefore, provide improved contact with the surface of the shaft 14 itself.

Although in this embodiment the apertures 48 are in the form of elongate slits, it will be appreciated that in other embodiments the apertures 48 may be a different shape, for example the apertures 48 may be in the form of circular holes or chevrons. Furthermore, the apertures 48 may be provided in both of the first and second parts 18, 20 of the main body 12 and the elastomeric material may be provided on the outer surfaces of both parts 18, 20 of the main body 12.

In use, a user locates the device 10 around an endoscope shaft 14 and engages the securing means 32 to close the main body 12. If no or only minimal pressure is applied to the main body 12, a clearance between a surface of the bore 16 of the main body 12 and the endoscope shaft 14 means that the device 10 can be slid along the length of the shaft 14. To grip the shaft 14, the user applies a gripping or pinching force to the device 10. This causes at least a part of the elastomeric material 44 to contact the shaft 14 through the apertures 48. When the pinching force is released the device 10 can be moved along the shaft 14, but remains attached to the shaft 14 due to the closed configuration of the main body 12 that surrounds the shaft 14.

In other preferred embodiments of a gripping device, elastomeric material is provided on an inner surface of the main body such that, when the gripping device is engaged around the endoscope, the elastomeric material contacts the endoscope shaft. Examples of such embodiments are shown in FIGS. 3 to 6.

Figure 3:
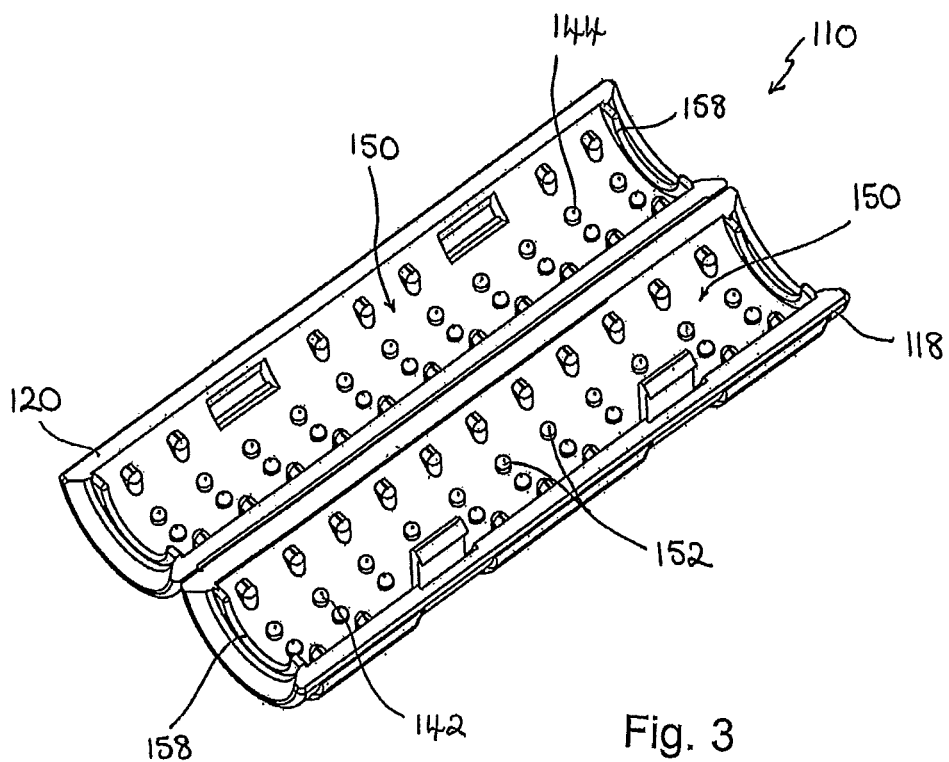
FIG. 3 is a perspective view of a gripping device according to a second preferred embodiment of the present invention in an open configuration.
Figure 4:
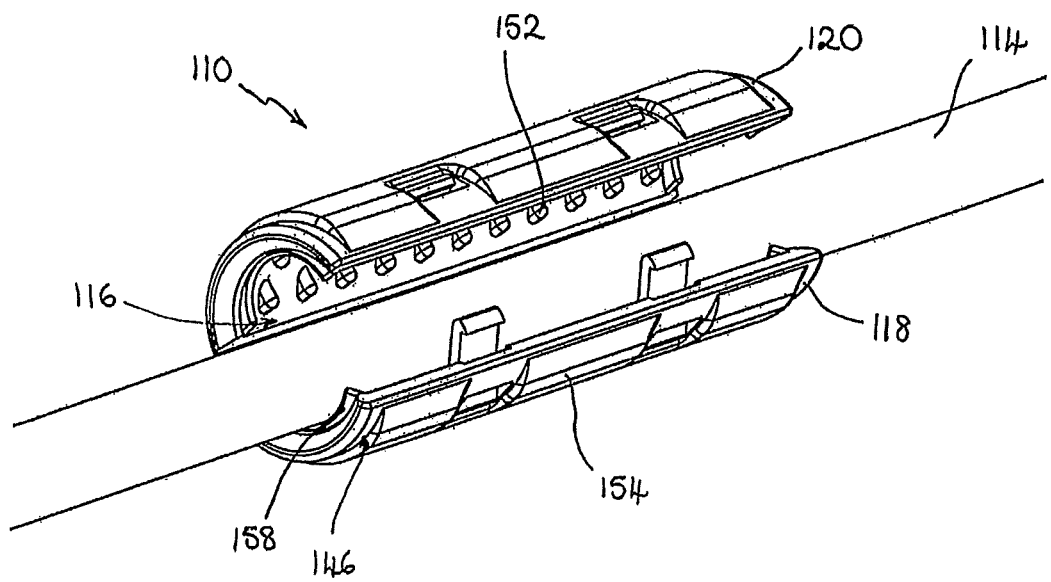
FIG. 4 is a perspective view of the gripping device of FIG. 3 partially closed around an endoscope shaft.

FIGS. 3 and 4 illustrate an embodiment in which the gripping means 142 comprises elastomeric material 144 provided on a first, inner surface 150 of each of the first and second parts 118, 120 as discrete protrusions 152 having a substantially circular or cylindrical shape. The embodiments shown in FIGS. 5 and 6 comprise gripping means 242, 342 in the form of discrete elastomeric protrusions 252, 352 on an inner surface 250, 350 of the first and second parts 218, 220, 318, 320 having a chevron shape. It will be appreciated that in other embodiments a continuous layer of elastomeric material may be provided on an inner surface of the first and second parts.

Figure 5:
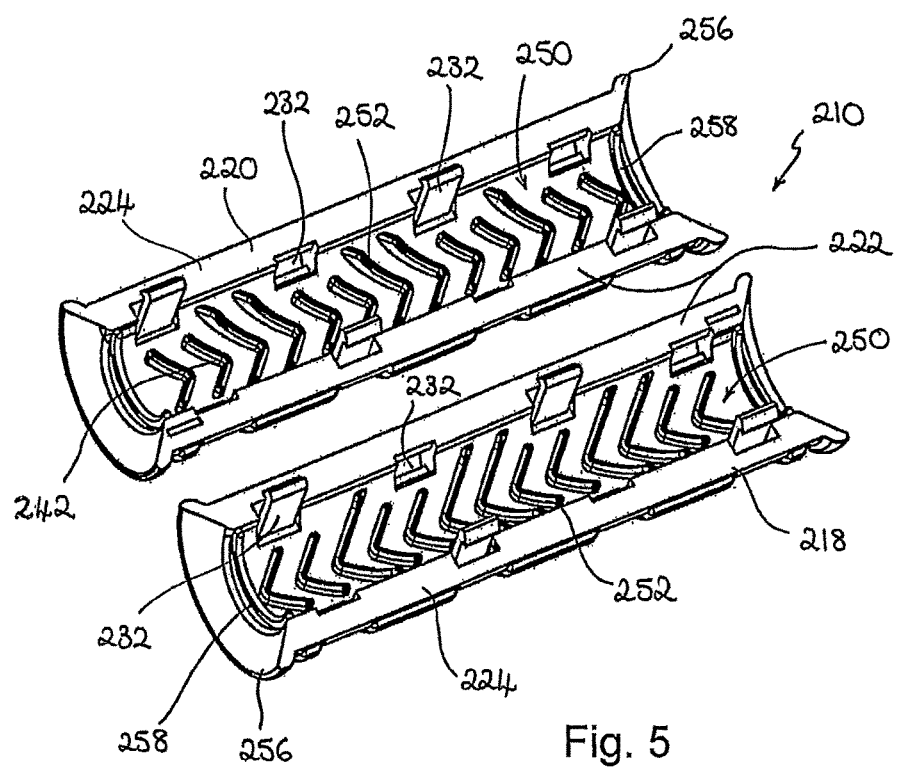
FIG. 5 is a perspective view of a gripping device according to a third preferred embodiment of the present invention in an open configuration.
Figure 6:
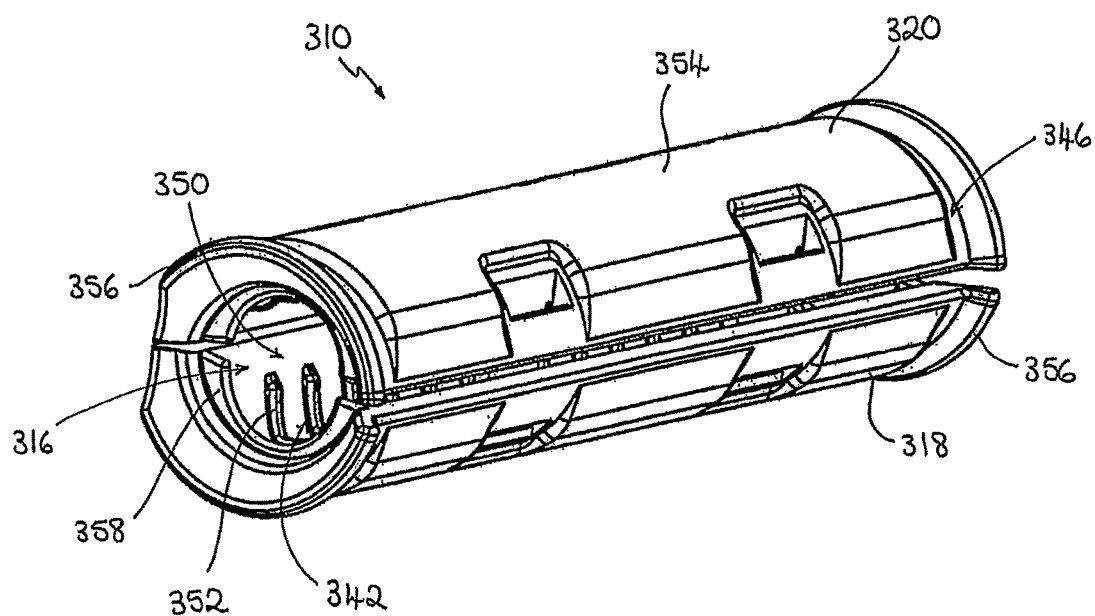
FIG. 6 is a perspective view of a gripping device according to a fourth preferred embodiment of the present invention in a closed configuration.
Figure 7:
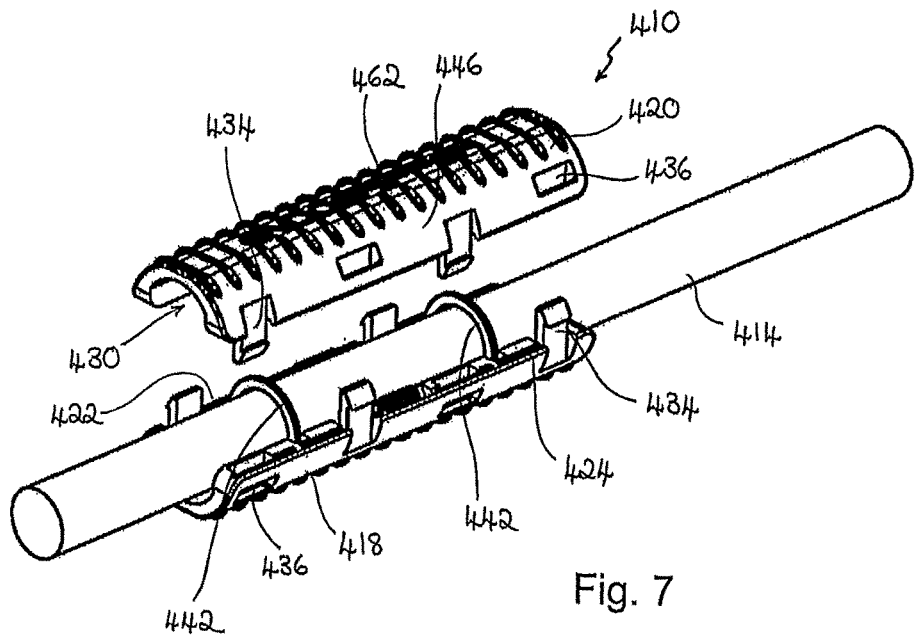
FIG. 7 is a perspective view of a gripping device according to a further preferred embodiment of the present invention in an open configuration.
Figure 8:
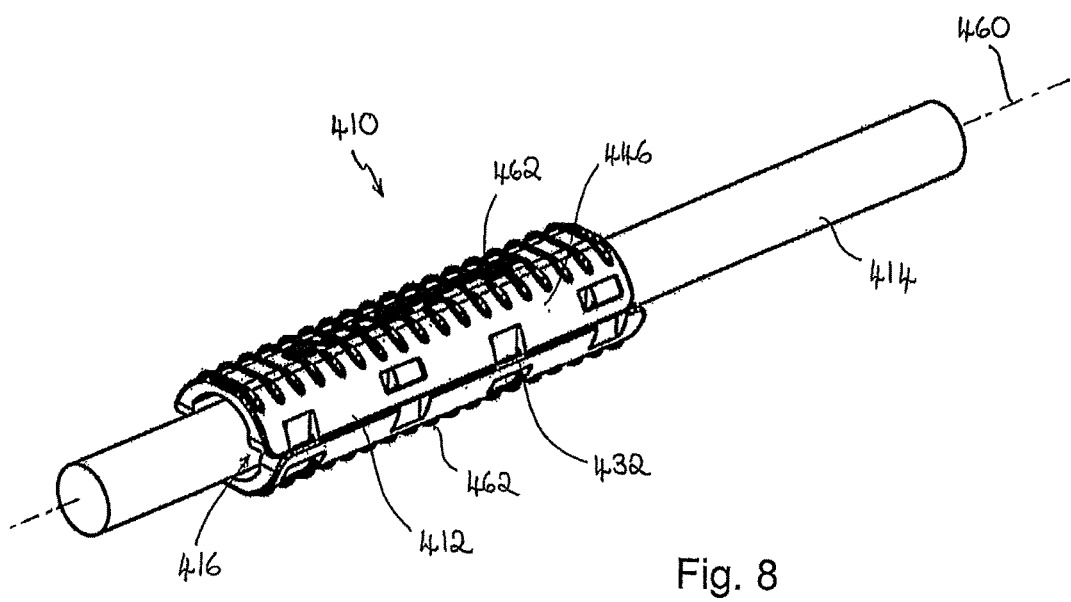
FIG. 8 is a perspective view of the gripping device of FIG. 7 in a closed and disengaged configuration around an endoscope shaft.

In the embodiment illustrated in FIG. 5, the first and second parts 218, 220 of the gripping device 210 are provided as two separate elements. As such, both of the first and second long edges 222, 224 of the first and second parts 218, 220 are provided with suitable securing means 232 to enable the parts 218, 220 to be secured together around an endoscope shaft. In this example, the device 210 preferably comprises biasing means to bias the first and second parts 218, 220 into a position in which there is a clearance between a bore of the device 210 and the endoscope shaft, such that no or minimal gripping force is applied to the shaft. In the embodiment shown in FIG. 6, the first and second parts 318, 320 are connected by means of a hinge along the first long edges and the hinge is configured such that no or minimal gripping force is applied to the endoscope shaft by the device 310 until a user applies a gripping force to the device 310.

It will be appreciated that, in further embodiments, the first and second parts may be permanently connected together along both of the two long edges, such that the device is installed around an endoscope shaft by sliding it over the end of the shaft. In these embodiments the device preferably comprises biasing means to bias the first and second parts into a position in which there is a gap between at least one of the pairs of long edges. The biasing means is preferably arranged such that the device has a first diameter to allow the device to be slid over the end of an endoscope shaft and, when a user grips the device, the biasing means allows the gap between the first and second parts to close, decreasing the diameter of the device and enabling the device to grip the shaft.

In all of the embodiments shown in FIGS. 3 to 6 a layer of elastomeric material 154, 354 is also provided on a second, outer surface 146, 346 of each of the first and second parts 118, 120, 318, 320. This outer layer of elastomeric material 154, 354 provides improved grip for a user's thumb and fingers on the device 110, 210, 310 during use.

In some embodiments one or more channels or cut-outs (not shown) may be formed through the outer layer of elastomeric material 154, 354. The channels are sized to receive a user's thumb or finger and are formed fully through the layer of elastomeric material 154, 354. In this way, when a user grips the device 110, 210, 310, their thumb and/or finger will make contact with the main body 112, 212, 312. Because the main body is made from a harder or stiffer material, greater feel or feedback of the forces experienced by the shaft is thereby provided to the user.

A key advantage of all of the above described gripping devices 10, 110, 210, 310 is that an outer diameter of the device is substantially greater than the outer diameter of the endoscope shaft 14, 114. Accordingly, less strain is caused to the muscles of a user's hand, wrist and forearm when they apply a pinching force to the gripping device 10, 110, 210, 310 compared to applying the same force to the endoscope shaft 14, 114 itself.

The increased diameter of the gripping devices 10, 110, 210, 310 and their installation around the lubricated endoscope shaft 14, 114 also means that the outer surface of the device 10, 110, 210, 310 is less likely to become coated with lubricant. This, therefore, allows the user to get an improved grip on the device 10, 110, 210, 310 compared to the lubricated surface of the shaft 14, 114. The possibility of the outer surface 46, 146, 346 of the device 10, 110, 210, 310 being covered in lubricant may be further minimised by provided a flared or flanged end 256, 356 at one or both ends of the device 210, 310. This flared or flanged end 256, 356, illustrated in the embodiments in FIGS. 5 and 6, comprises a radially outwardly projecting portion that minimises the amount of lubricant that may be pushed up over the surface of the device 210, 310 as the device is slid along the endoscope shaft.

Additionally, a better grip of the endoscope shaft is provided due to the gripping means 42, 142, 242, 342 of each of the devices 10, 110, 210, 310 being able to at least partially penetrate the layer of lubricant coating the endoscope shaft 14, 114 to grip the shaft directly. This advantage may be enhanced further by providing wiping means 158, 258, 358 at one or both ends of the device 110, 210, 310. The wiping means 158, 258, 358 preferably comprises a wiping element or blade 158, 258, 358 arranged to remove at least some of the lubricant from the shaft as the gripping device 110, 210, 310 is moved along the shaft during use. As illustrated in the embodiments shown in FIGS. 3 to 6, the wiping element 158, 258, 358 may be in the form of an annular blade 158, 258, 358 that extends into the bore 116, 316 of the device 110, 210, 310. The blade 158, 258, 358 does not contact the surface of the endoscope shaft, and the clearance between an edge of the blade 158, 258, 358 and the shaft means that not all of the lubricant is removed from the shaft but the amount of lubricant is reduced. The wiping element 158, 258, 358 is preferably formed from the same elastomeric material as the protrusions 152, 252, 352; however, in some embodiments the wiping element 158, 258, 358 may be made from a different material.

In all of the above described embodiments the elastomeric material is preferably a hydrophilic material. In other embodiments some or all of the elastomeric material may be a hydrophobic material. For example, the protrusions 152, 252, 352 may be made from a hydrophilic elastomeric material and the wiping element 158, 258, 358 may be made from a hydrophobic elastomeric material.

In other embodiments of the gripping device, the whole of the device may be made from a single elastomeric material, such that the device is in the form of a flexible sleeve or sheath that at least partially surrounds the endoscope shaft.

A further preferred embodiment of a gripping device 410 is illustrated in FIGS. 7 to 10. The gripping device 410 comprises a main body 412 that, in use, at least partially surrounds a shaft 414 of an endoscope to retain the device 410 on the shaft 414.

As in the first embodiment, the main body 412 is substantially cylindrical and includes a longitudinal bore 416 for receiving the shaft 414 of the endoscope. In this example the main body 412 comprises a first part 418 and a second part 420 that each has a half-pipe shape with a longitudinally extending channel 430 for receiving a part of the shaft 414. Parallel long edges 422, 424, therefore, extend between respective first and second ends of each of the first and second parts 418, 420.

Each of the first and second parts 418, 420 comprises securing means 432 for securing the main body 412 in a closed configuration. The securing means 432 are located proximate or along the long edges 422, 424 of each of the parts 418, 420. As shown most clearly in FIG. 7, the securing means 432 comprises a tab member 434 on one of the parts 418, 420 and a corresponding aperture 436 for receiving the tab member 434 on the other of the parts 418, 420. The tab members 434 and apertures 436 are configured such that, when engaged, the long edges 422, 424 of the first and second parts 418, 420 are in contact with each other such that the main body 412 fully surrounds the endoscope shaft 414.

In this example each of the long edges 418, 420 comprises two tab members 434 and two apertures 436; however, it will be appreciated that in other embodiments fewer or more tab members and apertures may be provided.

A width of each of the apertures 436 in a longitudinal direction is greater than a corresponding width of each of the tab members 434. As such, when the tab members 434 are engaged in the apertures 436, relative movement of the first and second parts 418, 420 is still possible along a longitudinal axis 460 due to sliding of the tab members 434 within the apertures 436.

A part of the outer surface 446 of each of the first and second parts 418, 420 includes gripping features 462, which in this example are in the form of ridges moulded in the outer surface 446 of the main body 412. The gripping features 462 improve a user's grip on the first and second parts 418, 420 enabling them to be easily slid relative to each other during use.

The gripping device 410 further comprises gripping means 442 in the form of a gripping element 464 having a substantially circular aperture. In this example the gripping element 464 comprises an O-ring. In other embodiments the gripping element 464 may be in the form of a plate or disc having an aperture. The plate or disc may be square or circular or any other suitable shape. The gripping element 464 ideally has a thickness that is substantially less than its width or diameter. A radius of the aperture lies within a plane of the gripping element 464, indicated by the dashed lines in FIGS. 9 and 10.

The main body 412 of the gripping device 410 comprises recesses 466 for receiving an edge portion of each of the gripping elements 464. A corresponding recess 466 is provided in the inner surface 450 of each of the first and second parts 418, 420 of the main body 412. Each recess 466 has a first side wall 468 that lies in a plane perpendicular to the longitudinal axis 460 and a second side wall 470 that lies at an angle to the first side wall 468 such that a width of the recess 466 is greater closer to the long edges 422, 424 of each of the first and second parts 418, 420.

Although the recesses 466 in each of the first and second parts 418, 420 are identical, when the first and second parts 418, 420 are connected together they are rotated 180° with respect to each other. In this way, the angled second side walls 470 of all of the recesses 466 lie in planes parallel to each other.

Figure 9:
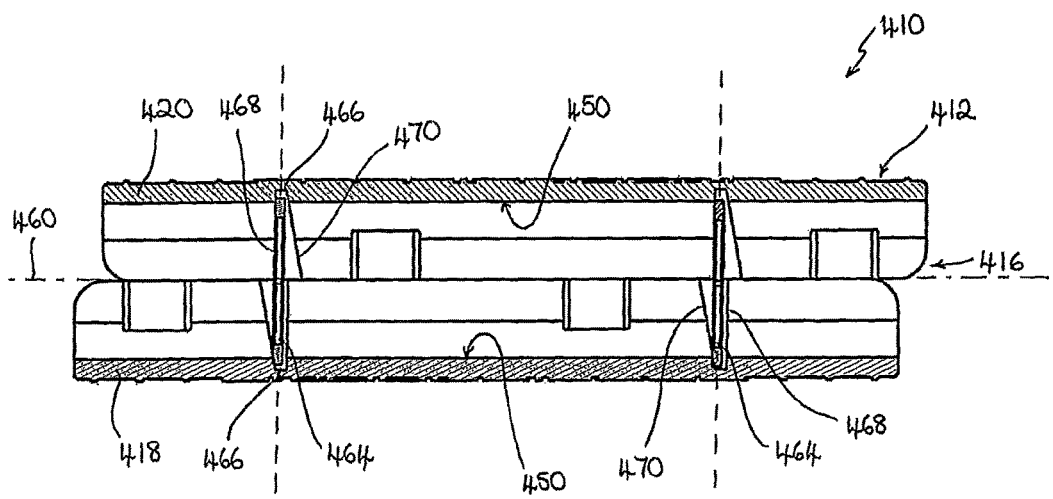
FIG. 9 is a longitudinal cross-sectional view of the gripping device of FIG. 8 in the disengaged configuration.
Figure 10:
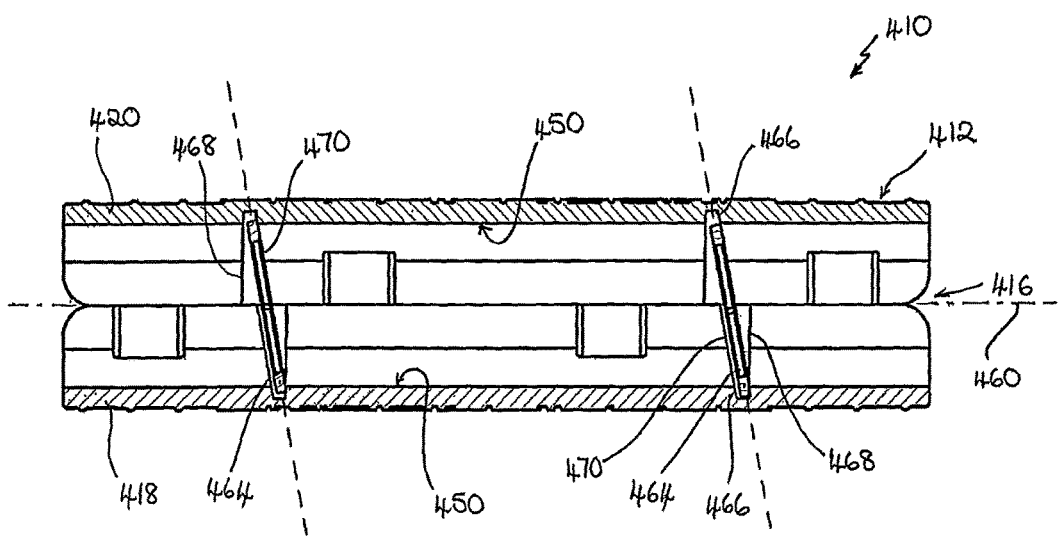
FIG. 10 is a longitudinal cross-sectional view of the gripping device of FIG. 8 in an engaged configuration.

The shape and configuration of the recesses 466 permits a gripping element 464 retained within the recesses 466 to be tilted with respect to the longitudinal axis 460 of the gripping device 410 as the first and second parts 418, 420 of the main body 412 are moved relative to each other as described above. In particular, when the first and second parts 418, 420 are in a first position with respect to each other, as illustrated in FIG. 10, the gripping element 464 is in contact with each of the second side walls 470 of the recesses. In this first position, the plane of the gripping element 464 is at a first angle with respect to the longitudinal axis 460. Typically this first angle will be less than 90°. When the first and second parts 418, 420 are in a second position with respect to each other, as illustrated in FIG. 9, the gripping element 464 is in contact with each of the first side walls 468 of the recesses 466. In this second position, the plane of the gripping element 464 is at a second angle with respect to the longitudinal axis 460. Typically this second angle will be about 90°, i.e. the plane of the gripping element 464 will be substantially perpendicular to the longitudinal axis 460. Importantly, the second angle is greater than the first angle.

In the first position the angle of the gripping element 464 is such that at least a part of the gripping element 464 around the aperture contacts the shaft 414 of the endoscope on opposing sides of the shaft. In particular, each of the second side walls 470 of the recesses 464 applies a force to the gripping element 464. A component of this force is in a direction perpendicular to the longitudinal axis 460 and this causes the gripping element 464 to apply a gripping force to the shaft 414. The angle of the second side walls 470 determines the magnitude of the gripping force that is applied to the shaft 414 and, in this way, the device 410 can be designed so that there is a limit to the force that is applied to the shaft 414 to prevent damage to the shaft. In the second position, each of the first side walls 468 of the recesses 466 applies a force to the gripping element 464. This force is applied in a direction substantially parallel to the longitudinal axis 460 and, therefore, no gripping force is applied to the shaft 414 and the device 410 can be easily moved along the shaft 414.

The gripping device 410 preferably includes biasing means to bias the first and second parts 418, 420 in the first position, such that the user must apply a force to the main body 412 to slide the first and second parts 418, 420 into the second position.

In use, the gripping elements 464 and main body 412 are located around the shaft 414 of the endoscope. The user applies a shearing force to the first and second parts 418, 420 to move them into a second position and slides the device 410 along the shaft 414 to the required position. Releasing the force on the first and second parts 418, 420 preferably causes them to return to the first position in which the device 410 grips the shaft 414. The user may then grip the device 410 in the traditional way that the shaft 414 would be gripped in order to manipulate the endoscope shaft.

Figure 11:
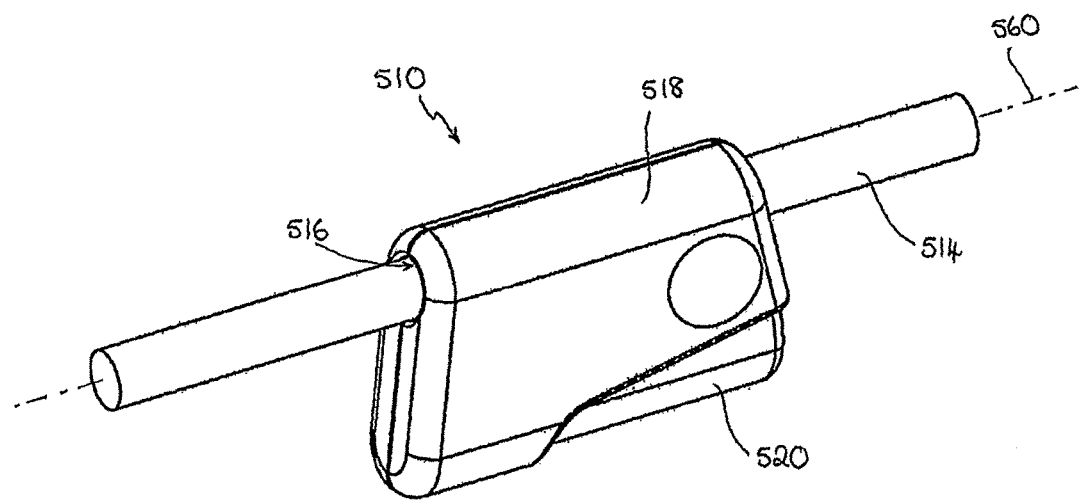
FIG. 11 is a perspective view of a gripping device according to a further embodiment of the present invention in an engaged configuration around an endoscope shaft.
Figure 12:
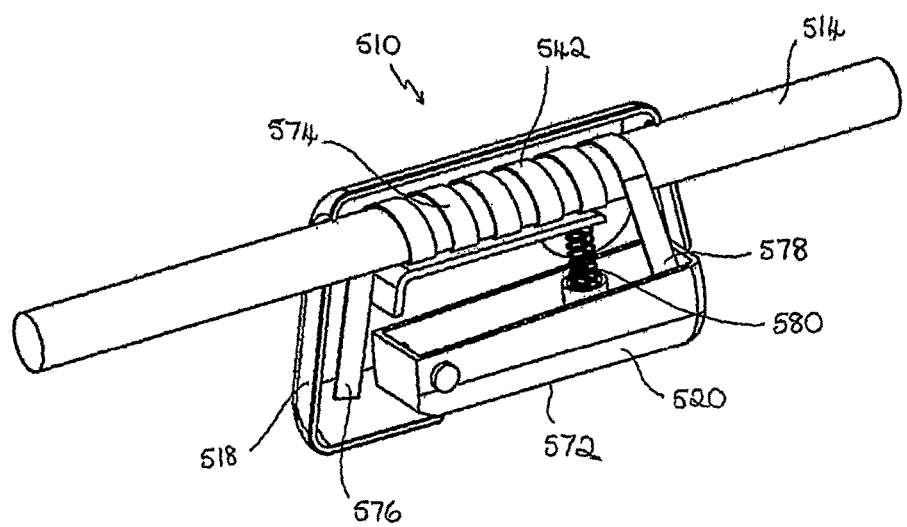
FIG. 12 is a cross-sectional view of the gripping device of FIG. 11 in the engaged configuration.

Another embodiment of a gripping device 510 is shown in FIGS. 11 and 12. The gripping device 510 comprises a first part 518 that has a bore 516 for receiving the endoscope shaft 514. The first part 518 has a substantially rectangular shape in cross-section perpendicular to a longitudinal axis 560 of the first part 518 and a substantially trapezoidal shape in cross-section parallel to the longitudinal axis 560. A second part 520 is pivotally attached to the first part 518 and forms a button or trigger 572.

Gripping means 542 comprises an elongate length of tape 574 or cord or other flexible member that is formed into a helical coil. A first end 576 of the tape 574 is attached to the first part 518 of the device 510 and a second end 578 of the tape 574 is attached to the second part 520 of the device 510. When the gripping means 542 is attached to an endoscope shaft 514 the shaft is received within and through the helical coil of the gripping means 542.

The second part 520 of the device 510 is movable relative to the first part 518 between a first position, when the button 572 is not pressed, and a second position, when the button 572 is depressed. In the first position the second part 520 applies a first tensile force to the second end 578 of the tape 574, and in the second position the second part 520 applies a second, reduced tensile force to the second end 578 of the tape 574. The reduced tensile force of the second position enables the radius of the helical coil to increase allowing the endoscope shaft 514 to be slid though the gripping means 542 by a user of the device 510. When the second part 520 returns to the first position, the tensile force on the tape 574 increases causing the radius of the helical coil to decrease, such that the gripping means 542 grips the endoscope shaft 514. Preferably the device 510 comprises biasing means 580, for example a spring 580, that biases the second part 520 in the first position.

Retaining means (not shown) may be provided in the first part 518 that engages with the gripping means 542 to maintain the substantially helical configuration of the tape 574, even when the second part 520 is moved to the second position.

In use, a user depresses the button or trigger 572 to move the second part 520 into the second position. The gripping device 510 can then be slid along the endoscope shaft 514 to the required position. When the user releases the button 572, the second part 520 moves back to the first position and the gripping means 542 grips the shaft 514. The user can then grip the device 510, without depressing the button 572, to manipulate the endoscope shaft 514.

Figure 13:
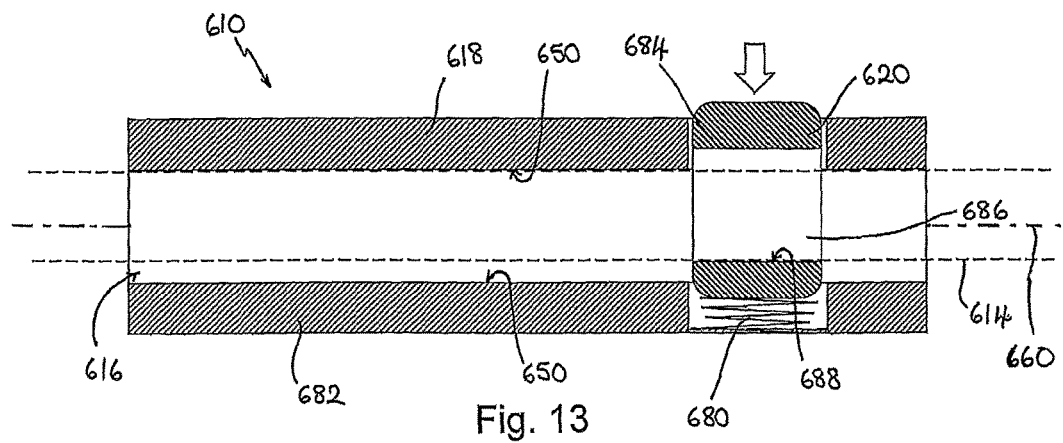
FIG. 13 is a longitudinal cross-sectional view of a gripping device according to a further embodiment of the present invention.
Figure 14:
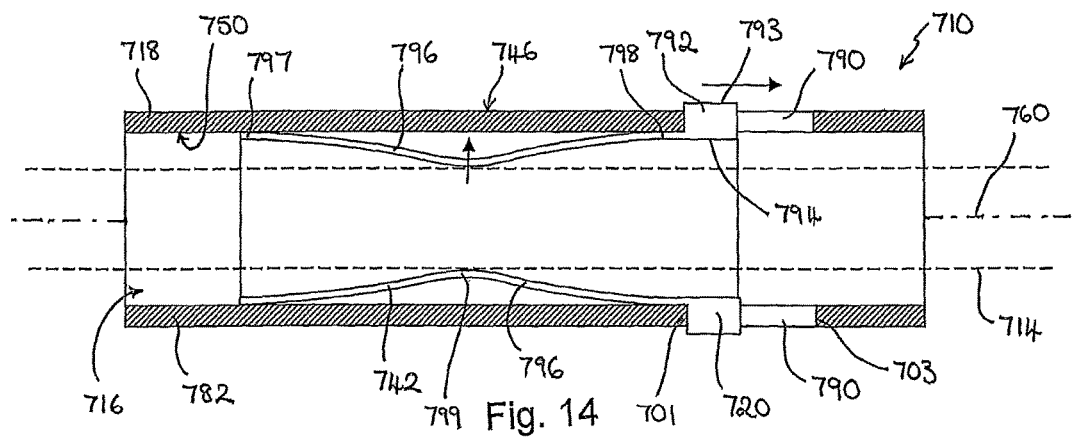
FIG. 14 is a longitudinal cross-sectional view of a gripping device according to another embodiment of the present invention.
Figure 15:
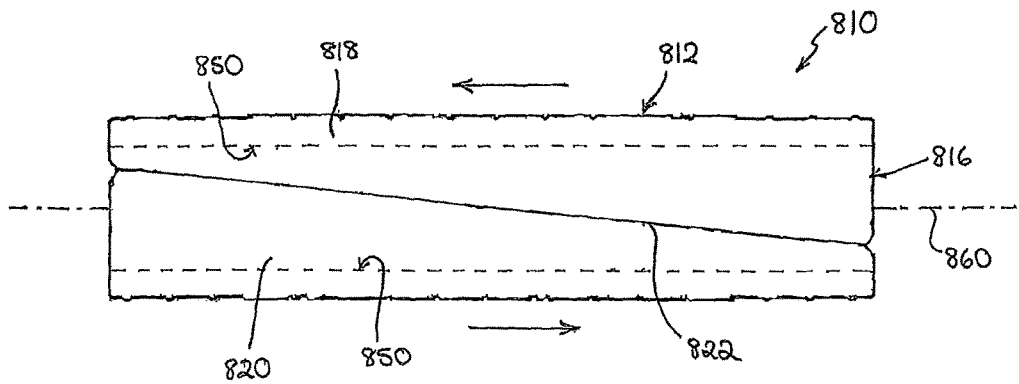
FIG. 15 is a side view of a gripping device according to a further embodiment of the present invention.

FIGS. 13 to 15 illustrate further possible embodiments of a gripping device of the present invention. In all of the embodiments the device comprises first and second parts that are movable relative to each other to cause gripping means to engage with an endoscope shaft.

In the embodiment shown in FIG. 13 the first part 618 of the device 610 comprises a cylindrical tube 682 having a longitudinal bore 616 for receiving the endoscope shaft 614. The second part 620 of the device 610 comprises a button member 684 that extends across the bore 616 of the first part 618. The button member 684 includes an aperture 686 having substantially the same diameter as the bore 616.

In a first position, illustrated in FIG. 13, a portion of the button member 684 extends into the bore 616 of the first part 618. In this position the endoscope shaft 614 is gripped between a portion of the surface 650 of the bore 616 and, on an opposite side of the shaft 614, a portion of the surface 688 of the button member 684 surrounding the aperture 686; these two opposing surfaces 650, 688 thereby forming the gripping means of the device 610.

In use, a user can depress the button member 684, as illustrated by the arrow in FIG. 13, to move the second part 620 relative to the first part 618 in a direction perpendicular to a longitudinal axis 660 into a second position. In this second position the aperture 686 is aligned with the bore 616 of the first part 618. The diameters of the bore 616 and the aperture 686 are greater than the outer diameter of the endoscope shaft 614 and, accordingly, in this second position the user can freely slide the device 610 along the shaft 614.

The device 610 further includes biasing means 680 in the form of a spring 680, that biases the button member 684 in the first position. In this way, the user can release the button and the button member 684 will return to the first position in which the device 610 grips the endoscope shaft 614.

In the embodiment of a gripping device 710 shown in FIG. 14 a first part 718 of the device 710 comprises a cylindrical tube 782 having a longitudinal bore 716 for receiving the endoscope shaft 714. At least one slot 790 is formed through a wall of the tube 782 extending in a direction parallel to a longitudinal axis 760. In this example two slots 790 are formed on opposing sides of the tube 782. A second part 720 of the device 710 comprises one or more slider members 792 that extend through the slot 790 such that a first side 793 of the slider member 792 protrudes from an outer surface 746 of the tube 782 and a second side 794 of the slider member 792 extends into the bore 716 of the tube 782.

Gripping means 742 in the form of resilient bands 796 or elongate members are positioned within the bore 716 of the tube 782 and extend generally in a direction parallel to the longitudinal axis 760 of the device 710. Each of the resilient bands 796 is curved or bowed such that first and second ends 797, 798 of the bands 796 are located proximate the inner surface 750 of the tube 782 and a central portion 799 of the band 796 extends inwards towards the centre of the bore 716 of the tube 782. A plurality of such bands 796 are positioned around the surface 750 of the bore 716 such that the inwardly bowed central portions 799 of the bands 796 together form a restriction in the bore 716.

All of the first ends 797 of the resilient bands 796 are connected to the first part 718 of the gripping device 710 so that they cannot move with respect to the tube 782. The second ends 798 of the resilient bands 796 are connected together and to the second part 720 of the device 710, i.e. the slider member 792.

As the slider member 792 is moved from a first end 701 of the slot 790 to a second end 703 of the slot 790, the central portion 799 of each of the resilient bands 796 is forced to move in an outward direction towards the inner surface 750 of the tube 782, as illustrated by the arrows in FIG. 14. This movement increases the diameter of the restriction in the bore 716 allowing the device 710 to be slid along the endoscope shaft 714. When the slider member 792 returns to the first end 701 of the slot 790, the resilient bands 796 bow inwards again and cause the central portion 799 of each of the bands 796 to grip the endoscope shaft 714.

In this example, as the slider member 792 is moved from the first end 701 of the slot 790 to the second end 703, the second ends 798 of the resilient bands 796 are pulled further away from the first ends 797 of the resilient bands 796 in a direction parallel to the longitudinal axis 760.

In other, similar embodiments, the gripping means may be in the form of a sleeve formed of helically woven bands positioned within the bore. In these embodiments, as the slider member is moved towards the second end of the slot, i.e. a second end of the woven sleeve is pulled further away from a fixed first end of the sleeve, the diameter of the sleeve decreases due to the weave of the bands. This principle is similar to that of Chinese finger trap devices. In other embodiments each end of the woven sleeve may be attached to a generally cylindrical tube, the cylindrical tubes being telescopically arranged and moveable with respect to each other.

FIG. 15 shows a further embodiment of a gripping device 810. The gripping device 810 comprises a main body 812 that, in use, at least partially surrounds a shaft of an endoscope to retain the device 810 on the shaft. The main body 812 is substantially cylindrical and includes a longitudinal bore 816 for receiving the shaft of the endoscope. In this example the main body 812 comprises a first part 818 and a second part 820 that each has a first end and a second end and long edges 822 that extend between the first and second ends. The long edges 822 are sloped such that they lie in a plane that is at an angle to the longitudinal axis 860 of the device 810.

When the first and second parts 818, 820 are secured together they remain movable relative to each other in a direction parallel to the longitudinal axis 860. Moving the first and second parts 818, 820 between a first position and a second position in directions indicated by the arrows in FIG. 15, causes the diameter of the bore 816 to increase due to the slope of the long edges 822. Similarly, moving the first and second parts 818, 820 back to the first position causes the diameter of the bore 816 to decrease again.

In this way, a user can apply a shearing force to the first and second parts 818, 820 to move them to the second position to enable the device 810 to be slid along the endoscope shaft. Applying an opposite force to the first and second parts 818, 820 to move them to the first position causes the inner surfaces 850 of the first and second parts 818, 820 to grip the shaft. In preferred embodiments the device 810 includes biasing means to bias the first and second parts 818, 820 in the first position.

In particularly preferred embodiments of the present invention the gripping device is single use. As such, the gripping device includes a feature that is configured such that, after the device has been removed from around an endoscope shaft, the device cannot be placed or retained around a second shaft.

In some embodiments the gripping device is designed to be removed from around an endoscope shaft by disengaging the securing means and at least partially separating the first and second parts. In these embodiments the single use feature may be a part of the securing means that is configured to break when the securing means are disengaged or separated to prevent them being re-engaged a second time.

In other embodiments the gripping device is designed to be slid off the end of the endoscope shaft after use. In these embodiments the single use feature may comprise means for preventing the device being slid back onto another shaft. For example, the single use feature may comprise resilient fingers that extend into the bore of the device when the device is removed from the shaft and prevent a second shaft being inserted into the bore.

An embodiment of a gripping device including such a single use feature is illustrated in FIGS. 16 to 21.

The gripping device 910 comprises a main body 912 that, in use, at least partially surrounds a shaft 14 of an endoscope (shown in FIGS. 20 and 21) to retain the device 910 on the shaft 14.

The main body 912 is substantially cylindrical or tubular and includes a longitudinal bore 916 for receiving the shaft 14 of the endoscope. In this example the main body 912 comprises a first part 918 and a second part 920 that are hingedly connected. Each of the first and second parts 918, 920 has a half-pipe shape, such that a cross-section perpendicular to a longitudinal axis of each part is substantially semi-circular. Parallel long edges 922, 924 extend between respective first and second ends 926, 928 of each of the first and second parts 918, 920. In this way, a channel 930 is formed in each of the first and second parts 918, 920 for receiving the endoscope shaft 14.

The first and second parts 918, 920 are hingedly connected along respective first long edges 922. In this example the hinge is a natural hinge formed in the material from which the main body 912 is made.

A part of an outer surface 946 of each of the first and second parts 918, 920 includes gripping features 962, which in this example are in the form of discrete protrusions. The gripping features 962 are preferably made from an elastomeric material and improve a user's grip on the first and second parts 918, 920.

Figure 16:
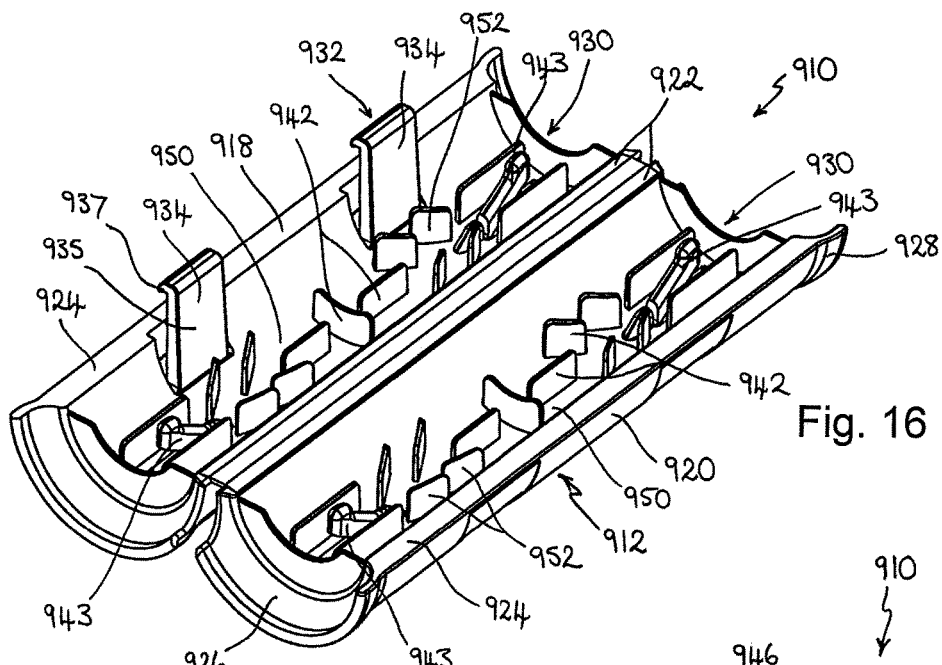
FIG. 16 is a perspective view of a gripping device according to a further embodiment of the present invention shown in an open configuration.
Figure 17:
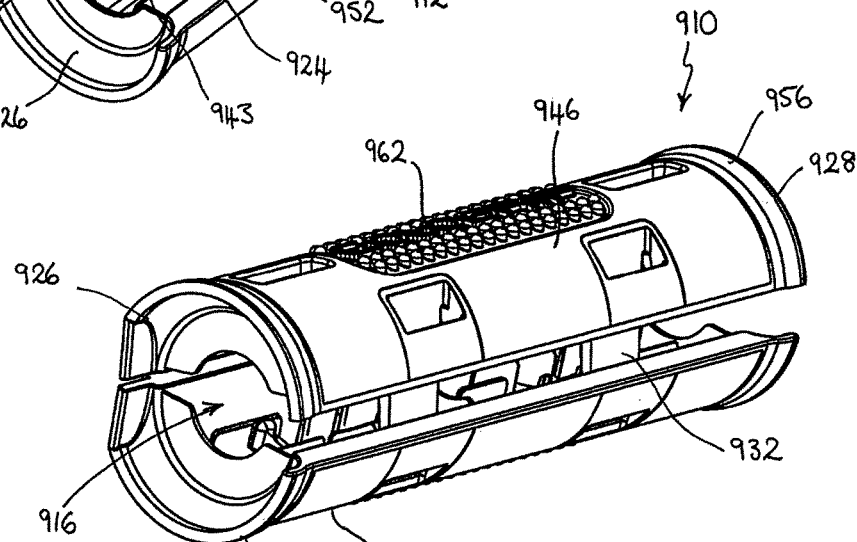
FIG. 17 is a perspective view of the gripping device of FIG. 16 shown in a first closed configuration.

The first and second parts 918, 920 are movable with respect to each other between a first, open configuration, shown in FIG. 16, and a second, closed configuration, shown in FIG. 17. In the open configuration an endoscope shaft 14 may be laid in one of the channels 930 and then the first and second parts 918, 920 may be closed around the endoscope shaft 14.

The first and second parts 918, 920 are retained in this closed position by securing or engaging means 932. In this embodiment the engaging means 932 comprises a pair of tabs 934 that protrude from the first part 918 proximate the second long edge 924. Each of the tabs 934 has a stem portion 935 and, at its distal end, a hook portion 937. The engaging means 932 further comprises a pair of apertures or recesses 936 formed in the second part 920 proximate the second long edge 924. A lip or edge of each of the recesses 936 comprises a hook portion 939. Each of the tabs 934 is positioned to engage with a corresponding one of the recesses 936, and the hook portions 937, 939 are configured such that, once the tabs 934 are engaged in the recesses 936, the hook portions 937, 939 prevent the tabs 934 being withdrawn from the recesses 936, as shown most clearly in FIG. 18.

In this way, the first and second parts 918, 920 cannot be returned to their first, open configuration without breaking a part of the engaging means 932. Accordingly, once the gripper device 910 has been engaged around an endoscope shaft 14, it can only be removed from the shaft 14 by sliding it along the length of the shaft 14 and off the end of the shaft.

Figure 18:
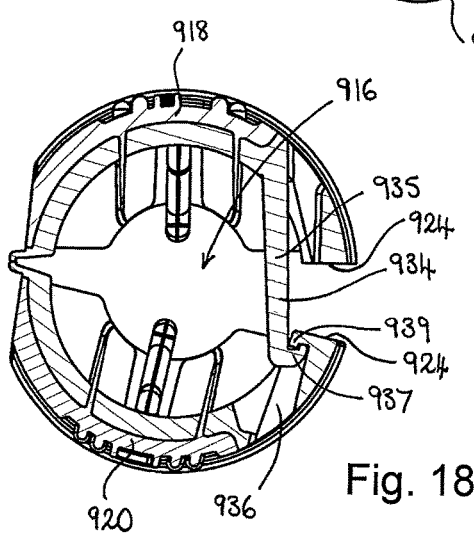
FIG. 18 is a cross-sectional view of the gripping device of FIG. 17 perpendicular to a longitudinal axis, with the gripping device in the first closed configuration.
Figure 19:
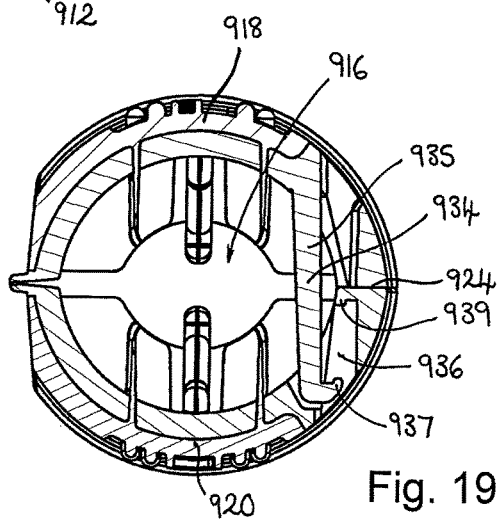
FIG. 19 is a cross-sectional view of the gripping device of FIG. 17 perpendicular to a longitudinal axis, with the gripping device in a second closed configuration.

The tabs 934 and recesses 936 are sized such that when the tabs 934 are engaged in the recesses 936 the first and second parts 918, 920 can still be moved with respect to each other between a first position, shown in FIG. 18, and a second position, shown in FIG. 19. In the first position there is a gap between the second long edges 924 of the first and second parts 918, 920. In this first position, the maximum distance between the second long edges 924 is limited by the engagement or mating of the hook portions 937, 939 of the tabs 934 and recesses 936, and the length of the stem portion 935 of each of the tabs 934. In the second position the second long edges 924 of the first and second parts 918, 920 are in touching contact. In preferred embodiments the first and second parts 918, 920 are biased in the first position.

Gripping means 942 in the form of a plurality of protrusions 952 are provided on an inner surface 950 of each of the first and second parts 918, 920, as shown most clearly in FIG. 16. The protrusions 952, therefore, extend into each of the respective channels 930, and radially inwardly into the bore 916 of the gripping device 910 when the gripping device 910 is in its closed configuration. In this embodiment the protrusions 952 are in the form of blades or fins and are made from an elastomeric material.

When the gripping device 910 is in the first position of the closed configuration, the gripping means 942 do not contact or only lightly contact a surface of the endoscope shaft 14 such that the gripping device 910 can be easily slid along the length of the shaft 14 by a user. When the user grips or squeezes the gripping device 910 to move it towards or into the second position of the closed configuration, the gripping protrusions 952 contact the surface of the shaft 14 of the endoscope more firmly, thereby imparting the gripping force to the endoscope shaft 14. Importantly the blade-like or fin-like shape of the protrusions 952 allows them to easily penetrate the layer of lubricant that typically coats the surface of the endoscope shaft 14.

As described above, once the gripping device 910 has been engaged around an endoscope shaft 14 it must then be removed by sliding it off the end of the shaft 14. In order to prevent the gripping device 910 being reused by sliding it onto the end of another endoscope shaft 14, this embodiment of the gripping device 910 comprises detent means 941.

The detent means 941 comprises arm members 943 that are biased to extend into the bore 916 of the gripping device 910. A first pair of arm members 943 is connected to the first part 918 of the main body 912 and an opposing second pair of arm members 943 is connected to the second part 920 of the main body 912. Each of the arm members 943 is integrally formed with the respective first or second part 918, 920 and is hingedly connected to the first or second part 918, 920 by means of a live hinge 945 at its proximal end.

When the gripping device 910 is initially moved from the open configuration to the closed configuration and clamped around an endoscope shaft 14, the circumferential surface of the shaft 14 contacts the arm members 943 and pushes them radially outwards against the biasing force.

Figure 20:
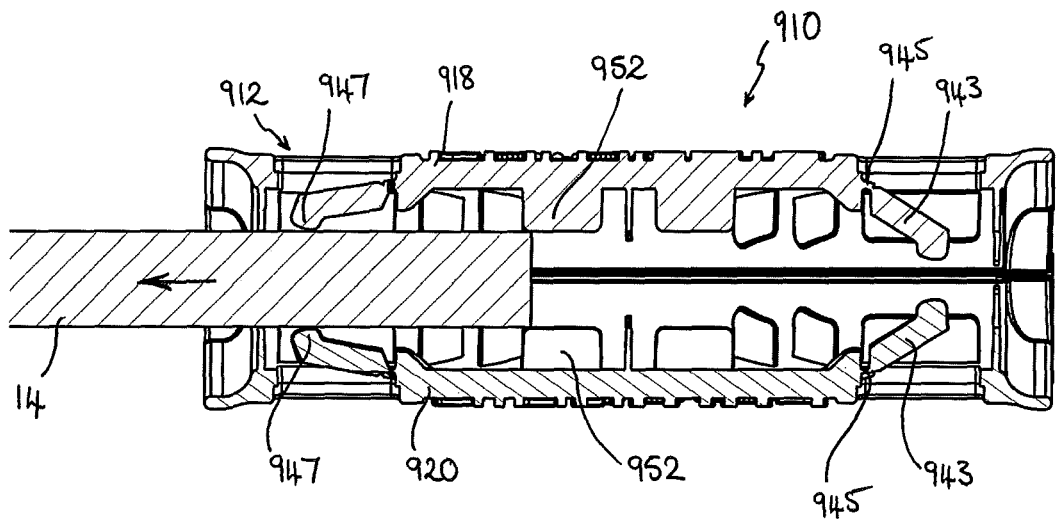
FIG. 20 is a longitudinal cross-sectional view of the gripping device of FIG. 17 showing an endoscope partially removed from the gripping device.
Figure 21:
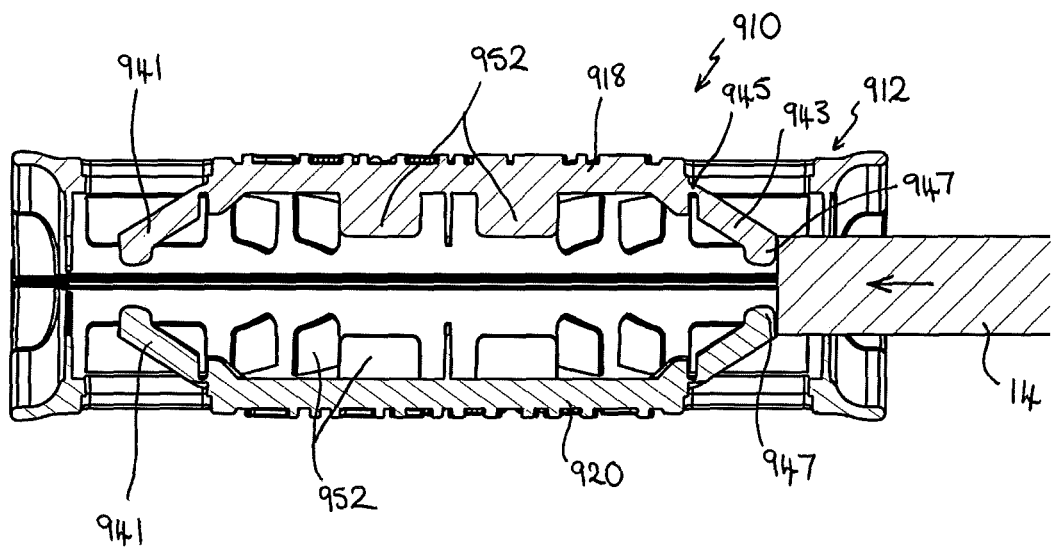
FIG. 21 is a longitudinal cross-sectional view of the gripping device of FIG. 17, the gripping device having been used and an endoscope partially inserted in one end.

When the endoscope shaft 14 is withdrawn from the gripping device 910, as illustrated in FIG. 20, the arm members 943 are biased such that a distal end 947 of each of the arm members 943 moves radially inwardly and extends into the bore 916 of the gripping device 910. In this way, when a user tries to insert another endoscope shaft 14 into the gripping device 910, as shown in FIG. 21, the arm members 943 contact an end or tip of the shaft 14 and prevent the shaft 14 being inserted fully through the bore 916 of the gripping device 910. In order to prevent an endoscope shaft 14 being inserted into the gripping device 910 in either longitudinal direction, the gripping device 910 preferably includes a first set of arm members 943 proximate the first end 926 of the main body 912 and arranged to extend in a direction substantially towards the first end 926, and a second set of arm members 943 proximate the second end 928 of the main body 912 and arranged to extend in a direction substantially towards the second end 928.

Some embodiments of the gripping device 910 of the present invention may further comprise an end cap 951. The end cap 951 comprises a cover portion 953 and securing means for releasably securing the end cap 951 to the main body 912 of the gripping device 910 such that the cover portion 953 substantially covers one end of the gripping device 910.

Figure 22:
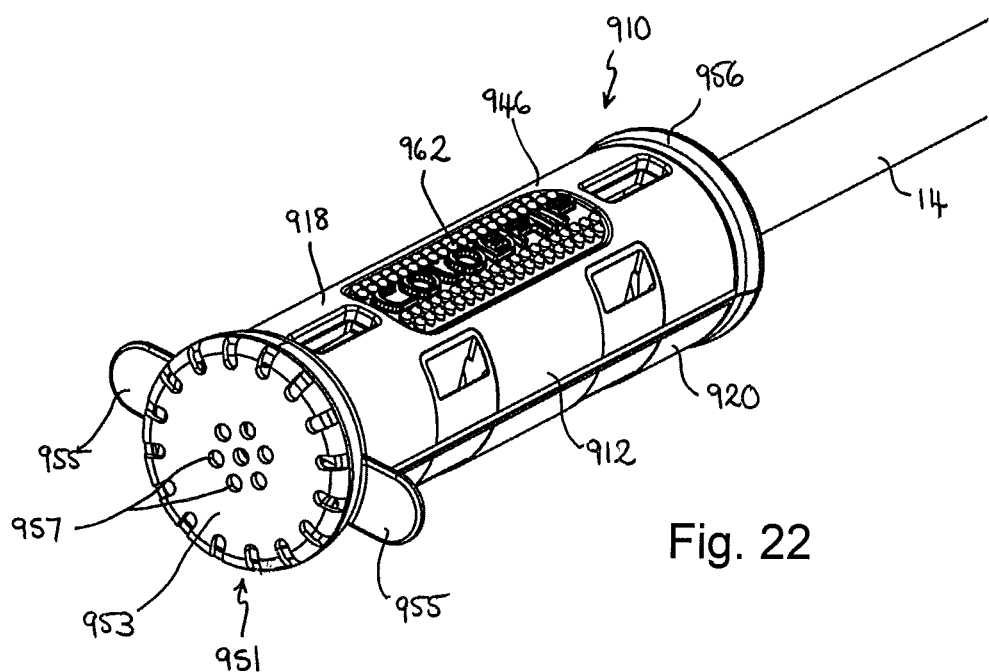
FIG. 22 is a perspective view of the gripping device of FIG. 17 showing an additional end cap of the device.
Figure 23:
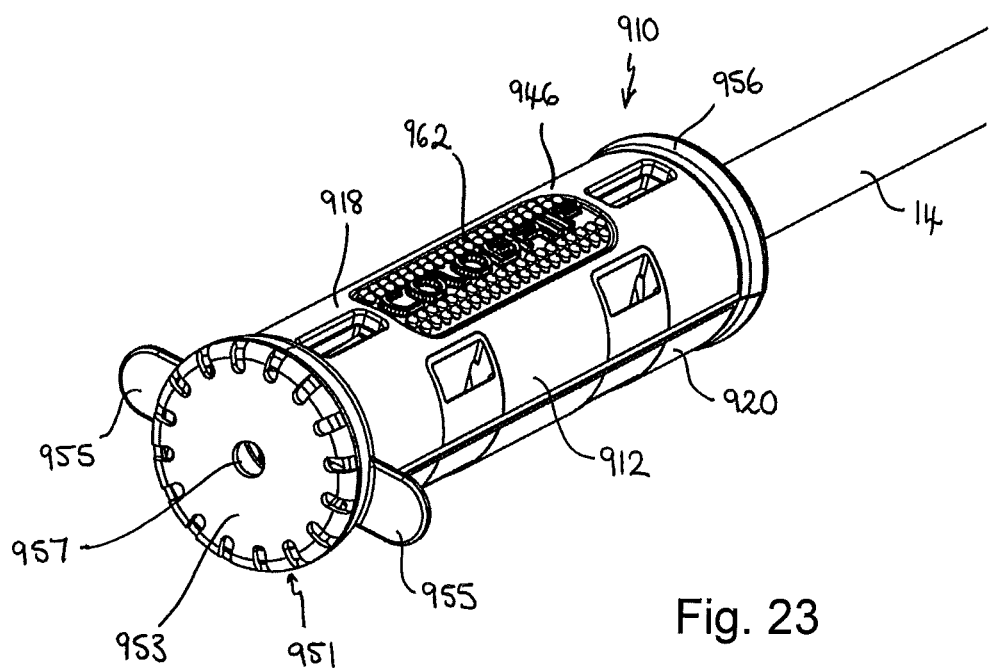
FIG. 23 is a perspective view of the gripping device of FIG. 22 showing an alternative design of end cap.

Two embodiments of a gripping device 910 including an end cap 951 are shown in FIGS. 22 and 23. In these embodiments the cover portion 953 is circular and the securing means comprises a lip (not shown) extending around the circumference of the cover portion 953. The lip is configured to engage with a flared end portion 956 of each of the first and second parts 918, 920 of the main body 912 of the gripping device 910. The end cap 951 is made from a resilient material so that the lip can be snapped over the flared end portions 956 to retain the end cap 951 on the main body 912.

The diameter of the cover portion 953 and/or lip is such that, when the end cap 951 is engaged with the end of the main body 912, the first and second parts 918, 920 of the main body 912 are retained in the closed configuration. Preferably the end cap 951 retains the first and second parts 918, 920 in the second position of the closed configuration such that the gripping device 910 grips the shaft 14.

In use the gripping device 910 is initially placed around the endoscope shaft 14 after the endoscope has been cleaned. The gripping device 910 is secured at the distal end of the shaft 14 by attaching the end cap 951, such that the main body 912 of the gripping device 910 extends over and protects the distal tip portion of the endoscope. When the endoscope is ready to be used, the end cap 951 is removed, and the gripping device 910 is slid along the endoscope shaft 14 in a direction away from the tip.

To remove the end cap 951 from the main body 912 a user simply pulls the end cap 951 to disengage the lip from around the flared portion 956. To aid in this removal, the end cap 951 preferably includes grip portions 955 in the form of lobes 955 that extend radially outwards from the cover portion 953. In these examples a pair of lobes 955 is provided. In use, a user can grip one or both of these lobes 955 to elastically deform the end cap 951 and pull the lip over the flared end portion 956.

Preferred embodiments of the end cap 951 further include one or more apertures or holes 957 in the cover portion 953. These holes 957 are sized to enable liquid to drain through the end cap 951, but are significantly smaller than the diameter of an endoscope shaft 14. In particular, these holes 957 enable liquid to drain from the endoscope if the endoscope is wet when the gripping device 910 is attached.

Although in the above embodiments the gripping device has been described as a device separate from the endoscope itself, it will be appreciated that a similar device may be incorporated into the structure of an endoscope shaft. In these embodiments of an endoscope, the gripping device remains permanently attached to the shaft of the endoscope, but may be slid along the length of the shaft and may be used to grip the shaft as described above.

In yet further embodiments the gripping device may form part of a glove, cloth or other element that is held or worn by the endoscopist. For example the first part of the gripping device may be attached to a finger portion of a glove and the second part of the device may be attached to a thumb portion of the glove.

The gripping device of the present invention, therefore, aids a user in gripping an endoscope shaft. In particular, the device of the present invention increases the diameter of the shaft that the user has to grip or pinch, thereby decreasing the stress and strain on the user's muscles. Furthermore, the device is designed to be retained around the endoscope shaft even when a user's grip on the device is released completely, making the device simple to handle and manipulate during a procedure, and the means provided for gripping the endoscope shaft and moving the gripping device along the shaft can be actuated with a single hand, such that use of the device does not require the user to change their traditional working methods.

The invention claimed is:

1. A single use gripping device for an endoscope shaft, the gripping device comprising:
   a first part;
   a second part, at least one of the first and second parts including a channel for receiving said shaft, the second part being moveable relative to the first part between a first, open configuration in which the endoscope shaft can be placed in the channel and a second, closed configuration in which, in use, the first and second parts surround and are retained around said endoscope shaft;
   a tab and a recess engageable to retain the first and second parts in said closed configuration, whereby the tab and recess are configured such that after the first and second parts have been engaged in the closed configuration, the first and second parts cannot be moved back to the open configuration without disabling the tab and recess;
   gripping protrusions provided on at least one of the first part and the second part, said protrusions configured such that when the gripping device is in its closed configuration the first and second parts are movable relative to each other between a first position in which the protrusions do not grip an endoscope shaft positioned in the channel to allow the gripping device to be slid along said shaft and a second position in which the protrusions grip said endoscope shaft; and
   arm members extending into said channel thereby preventing insertion of an endoscope shaft into said channel when the first and second parts are in the closed configuration, the endoscope shaft having a diameter such that the shaft is gripped by the protrusions when the first and second parts are in the second position.

2. A gripping device as claimed in claim 1, wherein the arm members are biased to extend into said channel.

3. A gripping device as claimed in claim 1, wherein said arm members are integrally formed with said first part or said second part.

4. A gripping device as claimed in claim 1, wherein the first and second parts define a main body of the device having first and second ends, and wherein a first arm member extends into said channel in a direction substantially towards said first end and a second arm member extends into said channel in a direction substantially towards said second end.

5. A gripping device as claimed in claim 1, wherein the first and second parts, in their closed configuration, form a substantially cylindrical main body of the device defining a longitudinal axis of the device, and wherein the first and second parts are hingedly connected along a longitudinal edge of each of the first and second parts.

6. A gripping device as claimed in claim 1, wherein said protrusions are made from an elastomeric material.

7. A gripping device as claimed in claim 1, wherein the first and second parts are biased in the first position.

8. A gripping device as claimed in claim 1, in which wherein the first and second parts, in their closed configuration, form a substantially cylindrical main body of the device having first and second ends, and the gripping device further comprises an end cap securable to said first end.

9. A gripping device as claimed in claim 8, wherein the end cap includes one or more holes sized to permit liquid to pass through said end cap.

10. An assembly comprising an endoscope and a gripping device as claimed in claim 1, the gripping device being secured around the shaft of the endoscope.

* * * * *